United States Patent [19]

Starzl et al.

[11] Patent Number: 5,196,437
[45] Date of Patent: Mar. 23, 1993

[54] METHOD FOR TREATING HEPATIC DISEASES AND REGENERATING LIVER TISSUE USING FK 506 AND RELATED COMPOUNDS

[75] Inventors: Thomas E. Starzl; Satoru Todo; Antonio Francavilla, all of Pittsburgh, Pa.

[73] Assignee: Fujisawa Pharmaceutical Company, Ltd., Osaka, Japan

[21] Appl. No.: 629,028

[22] Filed: Dec. 18, 1990

Related U.S. Application Data

[63] Continuation of Ser. No. 479,465, Feb. 13, 1990, abandoned.

[51] Int. Cl.[5] .................... A61K 31/44; A61K 31/40
[52] U.S. Cl. .................................. 514/294; 514/411; 514/838; 514/894
[58] Field of Search ................ 514/326, 63, 422, 294, 514/411, 838, 894

[56] References Cited

PUBLICATIONS

Ochiai, T. et al, Effect of a New Immunosuppressive Agent, FK 506, on Heterotopic Cardiac Allotransplantation in the Rat, Trans Proc 19:1284–86 (1987).
Starzl, T. E., et al. FK 506 for Liver, Kidney, and Pancreas Transplantation, Lancet 2:1000–1004 (1989).
Inagaki, K. et al, Effects of FK 506 and 15-Deoxyspergualin in Rat Orthotopic Liver Transplantation, Transplant Proceedings 21(1):1069–1071 (1989).
Mazzaferro V. et al, Studies of the Hepatotrophic Qualities of FK 506 and CyA, Transplantation Proc. 22(1 Suppl 1) (1990), pp. 93–95.
*The Lancet*, (1989), vol. II, pp. 1248–1249, "Augmentation of Rat Liver Regeneration by FK 506 Compared with Cyclosporin", A. Francavilla et al.

Primary Examiner—Allen J. Robinson
Assistant Examiner—Gary E. Hollinden
Attorney, Agent, or Firm—Oblon, Spivak, McClelland, Maier & Neustadt

[57] ABSTRACT

Macrolide compounds having the structure shown below

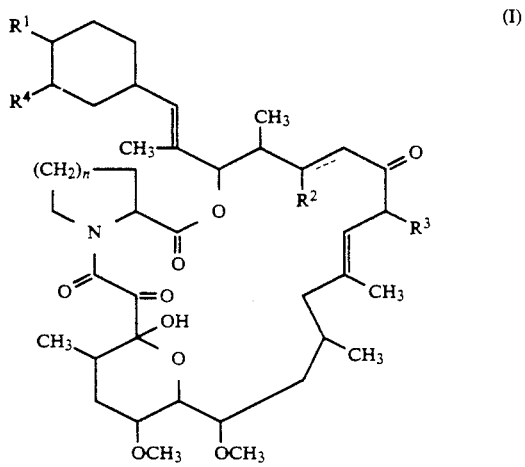

wherein $R^1$ is hydroxy or protected hydroxy, $R^2$ is hydrogen, hydroxy or protected hydroxy, $R^3$ is methyl, ethyl, propyl or allyl, $R^4$ is hydroxy, methoxy or oxo, n is 1 or 2 and the symbol of a line and a dotted is a single bond or a double bond, provided that $R^2$ is not protected hydroxy where $R^4$ is hydroxy or oxo are used to treat hepatic disease and regenerate liver tissue by facilitating hypertrophy and hyperplasia of hepatocytes.

32 Claims, No Drawings

METHOD FOR TREATING HEPATIC DISEASES AND REGENERATING LIVER TISSUE USING FK 506 AND RELATED COMPOUNDS

This application is a continuation of application Ser. No. 07/479,465, filed on Feb. 13, 1990, now abandoned.

BACKGROUND OF THE INVENTION

1. Field of the Invention

The invention relates to the use of macrolide compounds, such as FK 506, for treatment of liver diseases and for regeneration of liver tissue. More specifically, the invention relates to the use of macrolide compounds to promote liver hypertrophy and hyperplasia and thereby facilitate regeneration of liver tissue.

2. Discussion of the Background

Immunosuppressive agents such as azathioprine, adrenocortical steroids and cyclosporin are used to suppress the immune system during organ transplant operations. Azathioprine and the adrenocortical steroids are also known to depress the regeneration of liver tissue after partial hepatectomy (Gonzalez et al, Surgery, 1970, 68:254–59 and Guzek, Nature, 1964, 201:930-31). In contrast, cyclosporin facilitates hepatic regeneration in both rats and dogs. (Makowka et al, Surg Forum, 1986, 37:352-54; Kahn et al, Transplant Proc, 1988, 20 (Suppl 3):850-52; Kim et al, Surg Gynecol Obstet, 1988, 166:317-22; Mazzaferro et al, Surgery, in press.

Macrolide compounds, in particular the macrolide FK 506, are known immunosuppressive compounds which prevent acute and chronic liver allograft rejection in humans more reliably and completely than has been possible with previous compounds (Starzl et al, Lancet, 1989, 2:1000–1004). Several compounds belonging to this class of immunosuppressive macrolides are obtained from cultures of species belonging to the genus *Streptomyces*. Compounds within this class are described in U.S. patent application Ser. Nos. 06/799,855, filed Nov. 20, 1985, 06/868,749, filed May 30, 1986 and 07/386,233. filed Jul. 28, 1989.

The ability of immunosuppressive drugs to facilitate liver regeneration is important to patient survival following transplant operations. Liver restoration is also important in the recovery of liver tissue following severe liver disease. Accordingly, a need continues to exist for improved methods of facilitating liver regeneration.

SUMMARY OF THE INVENTION

Accordingly, one object of the present invention is to provide a method for enhancing the regeneration of liver tissue in mammals by administering to a mammal in need thereof a regeneration effective amount of a liver regenerating macrolide compound.

A further object is to provide a method for regenerating mammal liver tissue by facilitating or stimulating hypertrophy and hyperplasia of liver cells, i.e. hepatocytes.

A further object is to provide a method for treating hepatic disease, in particular hepatic disease having an autoimmune component.

These and other objects have been achieved by the present method in which a liver regenerating effective amount of a macrolide compound is administered to a mammal to facilitate hepatocyte, hypertrophy and hyperplasia.

DETAILED DESCRIPTION OF THE PREFERRED EMBODIMENTS

It has now been discovered that by administration of the immunosuppressive macrolide compounds of the present invention to a mammal, liver regeneration is facilitated by means of hypertrophy and hyperplasia of hepatocytes. The macrolide compounds of the present invention are therefore useful to treat liver diseases, particularly if there is an autoimmune component to the liver disease. Further, the macrolide compounds of the present invention are also effective in promoting hepatic healing even in the absence of immune system deficiencies, for example after hepatectomy.

The ability of the present compounds to regenerate liver tissue is surprising since many compounds which exhibit metabolic actions on the liver have no hepatotrophic actions. For example, glucagon which has a powerful metabolic effect on the liver does not have the hepatotrophic properties of the present macrolide compounds (Starzl et al, Lancet, 1976, 1:821-25).

Naturally occurring peptides, such as insulin and cytosolic hepatic stimulatory substance (HSS) exhibit hepatotrophic effects similar to those of the present compounds (Starzl et al, Lancet, 1976, 1:821-25; Starzl et al, Lancet, 1979, 1:127-130). However, the effect of the present macrolide compounds is somewhat greater than these naturally occurring peptides and furthermore they can be given orally instead of by infusion into the main vein (portal vein) supplying the liver with blood.

The present macrolide compounds are believed to modulate hepatocyte cellular growth either by means of their immunosuppressive action, by means of growth control effectors such as cytokines or through other mediators which are not necessarily directly linked to immunosupression. The hepatotrophic mechanism of the present compound is not known in detail. However, it is believed that the regeneration mechanisms take place substantially within the liver itself rather than systemically throughout the mammal. It is known, for example, that the macrolide FK 506 has no direct effect on hepatocytes in culture (Francavilla et al, Transplant Proc, in press). Therefore, intermediary substances or cells such as intrahepatic macrophages, endothelial cells or lymphoid aggregates may be involved.

The macrolide compounds useful in the present invention are compounds having structure I shown below.

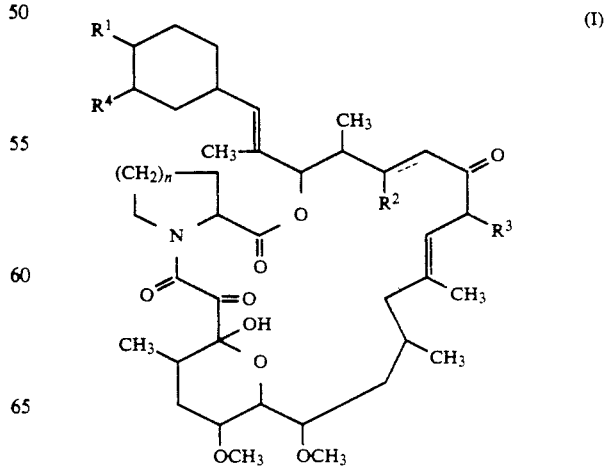

In structure I, $R^1$ is hydroxy or protected hydroxy, $R^2$ is hydrogen, hydroxy or protected hydroxy, $R^3$ is methyl, ethyl, propyl or allyl, $R^4$ is hydroxy, methoxy or oxo (=O), n is an integer of 1 or 2 and the symbol of a line and a dotted line is a single bond or a double bond, provided that $R^2$ is not protected hydroxy when $R^4$ is hydroxy or oxo, and salts thereof.

Such macrolide compounds may be prepared by both fermentation processes and synthetic organic processes as disclosed in U.S. application Ser. No. 06/799,855, filed Nov. 20, 1985 (U.S. Pat. No. 4,894,366); Ser. No. 868,749, filed May 30, 1986 and Ser. No. 07/386,233 filed Jul. 28, 1989. These U.S. patent applications are incorporated herein by reference for a more complete description of the compounds having structure I, their preparation and properties.

The term "lower" used in the specification is intended to mean 1 to 6 carbon atoms, unless otherwise indicated.

Suitable hydroxy-protective groups in the "protected hydroxy" may include: 1-(lower alkylthio) (lower) alkyl such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one is $C_1$-$C_4$ alkylthiomethyl and the most preferred one is methylthiomethyl; trisubstituted silyl such as tri(lower) alkylsilyl (e.g. trimethylsilyl, triethylsilyl, tributylsilyl, tert-butyl-dimethylsilyl, tri-tert-butylsilyl, etc.), lower alkyl-diarylsilyl (e.g. methyl-diphenylsilyl, ethyl-diphenylsilyl, propyl-diphenylsilyl, tert-butyl-diphenylsilyl, etc.), and the like, in which the preferred one is tri($C_1$-$C_4$) alkylsilyl and $C_1$-$C_4$ alkyl-diphenylsilyl, and the most preferred one is tert-butyl-dimethylsilyl and tert-butyl-diphenylsilyl; acyl such as aliphatic acyl, aromatic acyl and aliphatic acyl substituted with aromatic groups, which are derived from carboxylic, sulfonic and carbamic acids; and the like.

The aliphatic acyl may include lower alkanoyl which may have one of more suitable substituent(s) such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkyloxy(lower)alkanoyl which may have one or more suitable substituent(s) such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.), camphorsulfonyl, lower alkylcarbamoyl having one or more suitable substituent(s) such as carboxy and a protected carboxy, for example, carboxy(lower) alkylcarbamoyl (e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl such as tri(lower)alkylsilyl(lower)alkoxycarbonyl(lower)alkylcarbamoyl (e.g. trimethylsilylmethoxycarbonylethylcarbamoyl, trimethylsilylethoxycarbonylpropylcarbamoyl, triethylsilylethoxycarbonylpropylcarbamoyl, tertbutyldimethylsilylethoxycarbonylpropylcarbamoyl, trimethylsilylpropoxycarbonylbutylcarbamoyl, etc.), and the like.

The aromatic acyl may include aroyl which may have one or more suitable substituent(s) such as nitro (e.g. benzoyl, toluoyl, xyloyl, naphthoyl, nitrobenzoyl, dinitrobenzoyl, nitronaphthoyl, etc.), arenesulfonyl which may have one or more suitable subsitutent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and the like.

The aliphatic acyl substituted with aromatic group may include ar(lower) alkanoyl which may have one or more suitable substituent(s) such as lower alkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and the like.

The more preferred acyl group thus defined is $C_1$-$C_4$ alkanoyl which may have carboxy, cyclo($C_5$-$C_6$)-alkyloxy($C_1$-$C_4$)alkanoyl having two ($C_1$-$C_4$) alkyl groups on the cycloalkyl moiety, camphorsulfonyl, carboxy ($C_1$-$C_4$)-alkylcarbamoyl, tri($C_1$-$C_4$)alkylsilyl(-$C_1$-$C_4$)alkoxycarbonyl-($C_1$-$C_4$)alkylcarbamoyl, benzoyl which may have one or two nitro groups, benzenesulfonyl having halogens, phenyl($C_1$-$C_4$)alkanoyl having $C_1$-$C_4$ alkoxy and trihalo ($C_1$-$C_4$) alkyl, and the most preferred are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Particularly preferred macrolide compounds include:

(1) the macrolide compound in which $R^1$ and $R^2$ are each hydroxy, $R^3$ is allyl, n=2, and the symbol of a line and a dotted line is a single bond. This compound is known as FR-900506 or FK 506;

(2) the compound in which $R^1$ and $R^2$ are each hydroxy, $R^3$ is ethyl, n=2, and the symbol of a line and a dotted line is a single bond. This compound is also known as FR-900520 or WS 7238A;

(3) the compound in which $R^1$ and $R^2$ are each hydroxy, $R^3$ is methyl, n=2, and the symbol of a line and a dotted line is a single bond. This compound is known as FR-900523 or WS 7238B; and (4) the compound in which $R^1$ and $R^2$ are each hydroxy, $R^3$ is allyl, n=1 and the symbol of a line and a dotted line is a single bond. This compound is known as FR-900525.

With respect to the macrolide compounds (I) of this invention, it is to be understood that there may be one or more conformers or stereoisomeric pairs such as optical and geometrical isomers due to asymmetric carbon atoms and double bonds, and such isomers are also included within the scope of the present invention.

Salts of the macrolide compounds of the present invention include all pharmaceutically acceptable salts without limitation.

The macrolide compounds of the present invention may be administered as pure compounds or mixtures of compounds or preferably, in a pharmaceutical vehicle or carrier.

The pharmaceutical compositions of this invention can be used in the form of a pharmaceutical preparation, for example, in solid, semisolid or liquid form, which contains the macrolide compounds of the present invention, as an active ingredient, in admixture with an organic or inorganic carrier or excipient suitable for external, enteral, intravenous, intramuscular, or parenteral applications. The active ingredient may be compounded, for example, with the usual non-toxic, pharmaceutically acceptable carriers for tablets, pellets, capsules, suppositories, solutions (saline, for example), emulsions, suspensions (olive oil, for example), and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an effective amount sufficient to produce the desired effect upon the process or condition of the disease.

Mammals which may be treated using the method of the present invention include livestock mammals such as cows, horses, etc., domestic animals such as dogs, cats, rats, etc. and humans.

For applying this composition to a human, it is preferable to apply it by oral, parenteral, enteral, intravenous, or intramuscular administration. For promoting liver regeneration, the oral route is preferable. The compound is absorbed from the intestine and brought to the liver on first pass in high concentration. These macrolide compounds are the only liver regeneration promoting substances known which can be given by mouth and presented to the liver in this way and this is why they possess unique advantages for therapy. While the dosage of therapeutically effective amount of the macrolide compounds varies from and also depends upon the age and condition of each individual patient to be treated, a daily dose of about 0.01-1000 mg, preferably 0.1-500 mg and more preferably 0.5-100 mg, of the active ingredient is generally given for treating diseases and for regeneration of liver tissue, and an average single dose of about 0.2-0.5 mg, 1 mg, 5 mg, 10 mg, 50 mg, 100 mg, 250 mg and 500 mg is generally administered. Daily doses for chronic administration in humans will be in the range of about 0.3 mg/kg/day.

Other features of the invention will become apparent in the course of the following descriptions of exemplary embodiments which are given for illustration of the invention and are not intended to be limiting thereof.

EXAMPLES

Example 1 - Comparative Effect of Cyclosporin and FK 506 on Rat Liver Regeneration Adult male inbred Fisher 344 rats weighing 180-200 g were purchased from Hilltop Lab Animals Inc (Scottdale, Pa.). The animals were given standard rat laboratory diet and water ad libitum in a temperature and light controlled room (light 0730-1930). The rats were assigned to groups and treated for 4 days as controls or with cyclosporin or FK 506 (Table I). On the fourth day, between 0900 and 1030, the rats in groups 5-10 had a standard 40% or 70% hepatectomy under light ether aneasthesia. Animals in groups 3 and 4 had sham operations in which the liver was manipulated at laparotomy. Food and drink were allowed immediately. Parenteral fluid and electrolyte support were not required.

24 h after the hepatectomies, $185 \times 10^4$ Bq $^3$H-thymidine was administered to all rats by intraperitoneal injection. The rats, including groups 1 and 2, were killed 2 h later by guillotine. Extraction and purification of hepatic DNA were done with the method of Ove et al (Liver and hormones, New York: Raven Press, 1987:265-76) and DNA content was measured with calf thymus DMA (Sigma) as standard. Specimens from each liver were prepared for histological examination with hematoxylin and eosin and the proportion of hepatocytes in mitosis was counted. All results are means and SE.

As expected, DNA synthesis and the proportion of hepatocytes in mitosis were increased in rats with a 40% or 70% hepatectomy that were not given cyclosporin or FK 506 (groups 5, 7 and 8; Table II). After pretreatment for 4 days before hepatectomy with intramuscular FK 506 (groups 2, 4 and 10) or oral cyclosporin (group 9), regeneration was significantly augmented compared with controls. The effect was greater with FK 506 than with cyclosporin (group 10 compared with group 9). FK 506 did not increase resting hepatocyte mitosis or DNA synthesis. These indices were slightly increased in rats submitted to sham operation. When FK 506 was added to the sham operation group, hepatocyte mitosis and DNA synthesis were further and significantly increased.

TABLE I

| | | REGIMENS | | | |
|---|---|---|---|---|---|
| Group | Route | Cyclosporin (mg/kg) | FK 506 (mg/kg) | Vehicle* | Hepatectomy |
| 1 (n = 5) | IM | — | — | Saline | — |
| 2 (n = 5) | IM | — | 1 | Saline | — |
| 3 (n = 10) | IM | — | — | Saline | Sham |
| 4 (n = 10) | IM | — | 1 | Saline | Sham |
| 5 (n = 8) | IM | — | — | Saline | 40% |
| 6 (n = 8) | IM | — | 1 | Saline | 40% |
| 7 (n = 20) | PO | — | — | Olive oil | 70% |
| 8 (n = 20) | IM | — | — | Saline | 70% |
| 9 (n = 15) | PO | 10 | — | Olive oil | 70% |
| 10 (n = 15) | IM | — | 1 | Saline | 70% |

*250 μl saline or 200 μl olive oil.
IM = intramuscular, PO = oral.

TABLE II

EFFECTS OF CYCLOSPORIN AND FK 506 ON RAT LIVER REGENERATION (MEAN, SE)

| Group | $^3$H-thymidine incorporation ($\times 10^3$ cpm/mg DNA) | Proportion of hepatocytes in mitosis (%) |
|---|---|---|
| 1 | 3.3 (0.4) | 1.6 (0.1) |
| 2 | 3.2 (0.3) | 1.7 (0.1) |
| 3 | 4.9 (0.5) | 6.8 (0.6)+ |
| 4 | 10.5 (0.8)* | 9.5 (0.5)++ |
| 5 | 12.5 (1.3) | — |
| 6 | 32.4 (8.2)** | — |
| 7 | 138.1 (13.1) | 31.0 (2.0) |
| 8 | 130.0 (9.2) | 29.0 (2.8) |
| 9 | 179.0 (14.0)*** | 44.0 (2.1)*** |
| 10 | 242.0 (28.0)≠ | 59.0 (3.0)≠ |

Student's t test:
*$p < 0.005$ vs groups 1, 2 and 3.
**$p < 0.001$ vs group 5.
***$p < 0.05$ vs group 7.
≠$p < 0.01$ vs group 8.
+$p < 0.01$ vs groups 1 and 2.
++$p < 0.05$ vs groups 1 and 2.

Example 2 - Effects of FK 506 in Dogs

Twenty adult female beagle dogs underwent Eck fistula (Starzl et al, Lancet, 1976, 1:821-25). After performing a large side to side portacaval shunt, the left and right portal vein branches were ligated. A small infusion catheter was tied into the left branch and led through the abdominal wall and subcutaneously to a battery charged infusion pump that was incorporated into a non-restraining body cast. A constant infusion was started of the control or test fluids at the volume of 20 to 30 ml/day. Oral fluids and diet were allowed ad lib. Four days later, the animals were administered 0.2 mCi/kg (CH$_3$-$^3$H)-thymidine with specific activity of 80-90 Ci/MMol (New England Nuclear, Boston). Two hours later, the dogs were anesthetized and killed.

Specimens were taken from 2 of the right hepatic lobes and 2 of the left lobes, fixed in 10% buffered formalin, and stained using standard hematoxylin-eosin staining techniques.

Autoradiography was carried out using Ilford K5 nuclear track liquid emulsion and an exposure time of at least 30 days. The number of mitoses, as an index of hepatocyte regeneration, was determined by counting the number of $^3$H-thymidine labelled nuclei per 1000 hepatocytes. The size of individual hepatocytes (index of hypertrophy) was determined by tracing out a large number of midzonal liver cells projected on standard-thickness paper, cutting out the individual silhouettes and weighing each (Starzl et al, Surg Gynecol Obstet, 1973, 137:179-199). This method has been shown to be accurate for determining hepatocyte cell size and has been validated by planimetry and by studies of unicellular organisms, the size of which have been determined directly. In normal, unaltered dogs, about $1.6 \pm 0.4$ mitosis per 1000 hepatocytes are present in the liver, and midzonal hepatocytes are about $0.17 \pm 0.01$ size-units (Starzl et al, Lancet, 1979, 1:127-130). The exceptional reproducibility of these values and the small standard deviations make it easy to identify changes caused by operations such as Eck fistula, drugs, or other experimental variables.

For studies of the organelles, small cubes of each hepatic sample were taken for electron microscopy. The tissue was post-fixed in glutaraldehyde followed by osmic acid. After embedding in Polarbed. 812 resin, ultrathin sections were cut, stained with lead citrate and examined in a Philip's 300 electron microscope. Measurements of the organelles were made on electron micrographs by Loud's method (Loud, J Cell Biol, 1968, 37:27-46).

Results are expressed as mean±standard deviation (SD). The Student's t-test was employed in individual experimental groups to compare differences between right and left lobes or between groups. A p value less than 0.05 was considered to be significant.

Infusion of the drug vehicle did not effect the hepatocyte atrophy typical of the Eck fistula liver or change the low grade hyperplasia (Table III, vehicle controls). However, when FK 506 was infused into the left portal vein, atrophy of the left lobar hepatocytes was prevented in proportion to the dose, and the rate of mitoses was increased. These changes were significantly greater in the directly infused lobes at all doses, but even the non-infused lobes were significantly effected compared to the vehicle controls at the high FK 506 doses (Table III).

Comparison of the ultrastructure of the left and right lobar hepatocytes showed that the hepatocytes exposed to infused FK 506 were almost normal even at the smallest doses (Tables IV and V). The amount of rough endoplasmic reticulum was restored relative to controls; in addition, dilatation and disruption of the cisternae were minimal. The number of microbodies, lysosomes and small lipid containing vacuoles were near normal levels in the FK 506-infused lobes. The mitochondria in these lobes were neither enlarged (Table V) nor abnormal.

The changes in the hepatocytes in the right lobes did not differ greatly from those seen in the controls at low doses of FK 506. However, at the 1 mg/kg/day dose, there was better preservation of the RER in the right lobes compared to right lobar hepatocytes in the vehicle controls (Table IV), and reduced lipid accumulation ($p<0.001$). At this high dose, the right lobar hepatocytes also had reduced microbodies ($p=0.07$) and lysosomes ($p<0.05$).

Example 3

| | |
|---|---|
| FK 506 | 1 g |
| Hydroxypropyl methylcellulose 2910 (TC-5R) | 1 g |
| Lactose | 2 g |
| Croscarmellose sodium (Ac-Di-Sol) | 1 g |

The FK 506 (1 g) was dissolved in ethanol (10 ml), and thereto was added hydroxypropyl methylcellulose 2910 (TC-5R) (1 g) to prepare a suspension. To this suspension was added dichloromethane (5 ml) to prepare a homogeneous solution. Lactose (2 g) and croscarmellose sodium (Trade Mark: Ac-Di-Sol, maker: Asahi Chemical Industry) were homogeneously suspended to this solution, and then the organic solvent was removed by evaporation. The residual product was dried under reduced pressure for 10 hours by vacuum dryer, milled for 2 minutes by coffee mill and then passed through a sieve (32 mesh) to give the solid dispersion composition of FK 506 (5 g). This composition was capsulated by a conventional manner to provide capsules containing 1 mg or 5 mg of FK 506 per each capsule.

There was no evidence of drug toxicity in the lobes infused with FK 506.

Human diseases for which the present macrolide compounds may be useful for their regeneration promoting properties include but are not limited to:

A. Postoperative patients after partial liver resection.

B. Acute liver necrosis caused by: (a) toxins, (b) viral hepatitis, (c) shock, (d) anoxia and (e) unknown causes.

C. Autoimmune liver diseases which are chronic including: (a) autoimmune hepatitis, (b) primary biliary cirrhosis, and (c) sclerosing cholangitis.

D. Chronic liver diseases without an autoimmune hepatitis including: (a) B-virus hepatitis, (b) non A/non B hepatitis, (c) alcoholic cirrhosis, and (d) cirrhosis of unknown etiology.

TABLE III

| FK-506 mg/kg/day | N* | Hepatocytes Size Units Left | p Left vs Right | Right | Left p vs. Vehicle | Right | Labeled Hepatocytes/ 1000 Hepatocytes Left | p Left vs Right | Right | Left p vs. Vehicle | Right |
|---|---|---|---|---|---|---|---|---|---|---|---|
| Vehicle | 6 | .114 +/− .007 | 0.4355 | .112 +/− .011 | | | 4.45 +/− .26 | 0.8429 | 4.42 +/− .24 | | |
| 0.01 | 12 | .111 +/− .008 | 0.0004 | .100 +/− .007 | 0.5782 | 0.1860 | 5.43 +/− .35 | 0.0167 | 4.77 +/− .60 | 0.0044 | 0.2477 |
| 0.1 | 12 | .137 +/− .008 | 0.0000 | .113 +/− .006 | 0.0065 | 0.8351 | 5.98 +/− .43 | 0.0001 | 5.19 +/− .38 | 0.0005 | 0.0086 |
| 1.0 | 10 | .162 +/− .012 | | .134 +/− .006 | 0.0004 | 0.0503 | 9.13 +/− .89 | | 5.37 +/− .78 | 0.0001 | 0.0510 |

TABLE III-continued

| | | Hepatocytes Size Units | | | | Labeled Hepatocytes/ 1000 Hepatocytes | | | |
|---|---|---|---|---|---|---|---|---|---|
| | | Left | Right | Left | Right | Left | Right | Left | Right |
| FK-506 mg/kg/day | N* | p Left vs Right | | p vs. Vehicle | | p Left vs Right | | p vs. Vehicle | |
| | | 0.0009 | | | | 0.0015 | | | |

*In each experiment, samples were taken from 2 different right lobes and 2 different left lobes. The n represents both samples and the number of animals is $\frac{n}{2}$

TABLE IV

| | | Area ($uM^2$) of endoplasmic reticulum (ER) per average midzonal hepatocyte | | | | | | | |
|---|---|---|---|---|---|---|---|---|---|
| | | Rough ER | | | | Smooth ER | | | |
| | | Left | Right | Left | Right | Left | Right | Left | Right |
| FK-506 mg/kg/day | N* | p Left vs Right | | p vs. Vehicle | | p Left vs Right | | p vs. Vehicle | |
| Vehicle | 3 | 13874 +/− 1221 | 13882 +/− 975 | | | 26416 +/− 3787 | 26680 +/− 2202 | | |
| | | 0.9672 | | | | 0.7996 | | | |
| 0.01 | 6 | 26332 +/− 1483 | 18697 +/− 1010 | 0.0000 | 0.0019 | 18433 +/− 535 | 23337 +/− 902 | 0.0661 | 0.1092 |
| | | 0.0001 | | | | 0.0000 | | | |
| 0.1 | 6 | 29889 +/− 1117 | 20325 +/− 975 | 0.0001 | 0.0007 | 18688 +/− 498 | 22747 +/− 1305 | 0.0703 | 0.0725 |
| | | 0.0001 | | | | 0.0018 | | | |
| 1.0 | 5 | 32091 +/− 1225 | 20839 +/− 1612 | 0.0000 | 0.0003 | 17876 +/− 642 | 23154 +/− 193 | 0.0574 | 0.0858 |
| | | 0.0002 | | | | 0.0024 | | | |

*One sample from a right lobe and one from a left lobe were studied. N is the number of animals.

TABLE V

| | | Organelle Volume ($uM^3$) in average midzonal hepatocytes | | | |
|---|---|---|---|---|---|
| | | Mitochondria | | Microbodies | |
| | | Left | Right | Left | Right |
| FK-506 mg/kg/day | N* | p Left vs Right | | p Left vs Right | |
| Vehicle | 3 | 1.86.3 +/− 506.4 | 1657.6 +/− 164.5 | 207.0 +/− 22.6 | 188.6 +/− 18.5 |
| | | 0.7683 | | 0.0288 | |
| 0.01 | 6 | 1233.7 +/− 222.4 | 1429.5 +/− 331.2 | 99.2 +/− 11.8 | 173.8 +/− 39.6 |
| | | 0.1903 | | 0.0080 | |
| 0.1 | 6 | 1288.5 +/− 236.2 | 1439.3 +/− 115.4 | 86.3 +/− 11.5 | 172.5 +/− 34.2 |
| | | 0.2529 | | 0.0025 | |
| 1.0 | 5 | 1284.8 +/− 178.9 | 1440.6 +/− 318.7 | 94.2 +/− 10.4 | 136.6 +/− 41.3 |
| | | 0.1996 | | 0.1111 | |
| | | Lysosomes | | Lipids | |
| | | Left | Right | Left | Right |
| FK-506 mg/kg/day | N* | p Left vs Right | | p Left vs Right | |
| Vehicle | 3 | 229.0 +/− 62.7 | 208.0 +/− 29.1 | 94.0 +/− 16.7 | 98.0 +/− 8.5 |
| | | 0.6660 | | 0.6883 | |
| 0.01 | 6 | 62.3 +/− 15.1 | 162.6 +/− 48.9 | 23.3 +/− 8.8 | 81.0 +/− 15.1 |
| | | 0.0017 | | 0.0012 | |
| 0.1 | 6 | 59.6 +/− 15.6 | 187.6 +/− 14.8 | 22.8 +/− 6.7 | 83.8 +/− 19.7 |
| | | 0.0000 | | 0.0011 | |
| 1.0 | 5 | 48.8 +/− 10.9 | 160.0 +/− 23.8 | 15.6 +/− 2.8 | 47.8 +/− 11.3 |
| | | 0.0002 | | 0.0044 | |

Obviously, numerous modifications and variations of the present invention are possible in light of the above teachings. It is therefore to be understood that within the scope of the appended claims, the invention may be practiced otherwise than as specifically described therein.

What is claimed as new and desired to be secured by letters patent of the United States is:

1. A method of regenerating mammal liver tissue, comprising administering to a mammal in need thereof a regeneration effective amount of a macrolide of formula I:

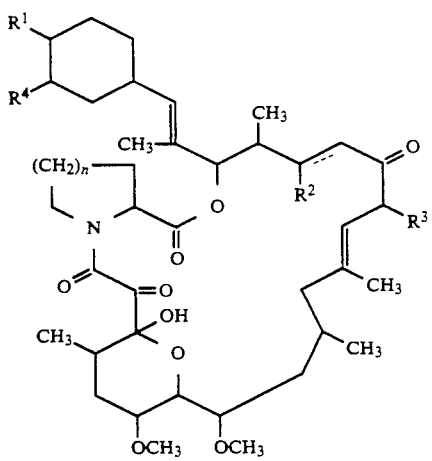 (I)

where $R^1$ is hydroxy or pharmaceutically acceptable protected hydroxy, $R^2$ is hydrogen, hydroxy or pharmaceutically acceptable protected hydroxy, $R^3$ is methyl, ethyl, propyl or allyl, $R^4$ is hydroxy, methoxy or oxo, n is 1 or 2 and the symbol of a line and a dotted line is a single bond or a double bond, provided that $R^2$ is not pharmaceutically acceptable protected hydroxy where $R^4$ is hydroxy or oxo, wherein said pharmaceutically acceptable protected hydroxy is selected from the group consisting of 1-(lower alkylthio)(lower)alkoxy, tri(lower)alkylsilyloxy, lower alkyl-diphenylsilyloxy, pharmaceutically acceptable organic carboxylic acyloxy, pharmaceutically acceptable organic sulfonic acyloxy and pharmaceutically acceptable organic carbamic acyloxy, and salts thereof.

2. The method of claim 1, wherein $R^1$ and $R^2$ are each hydroxy.

3. The method of claim 2, wherein $R^3$ is allyl.

4. The method of claim 1, wherein $R^3$ is ethyl.

5. The method of claim 1, wherein $R^3$ is methyl.

6. The method of claim 1, wherein $R^4$ is hydroxy.

7. The method of claim 1, wherein $R^4$ is methoxy.

8. The method of claim 1, wherein $R^4$ is oxo.

9. The method of claim 3, wherein the macrolide is FK 506.

10. The method of claim 1, wherein said administering is oral administration.

11. A method of stimulating hypertrophy and hyperplasis of hepatocytes, comprising contacting mammalian hepatocytes with an effective amount of a macrolide of the formula shown below:

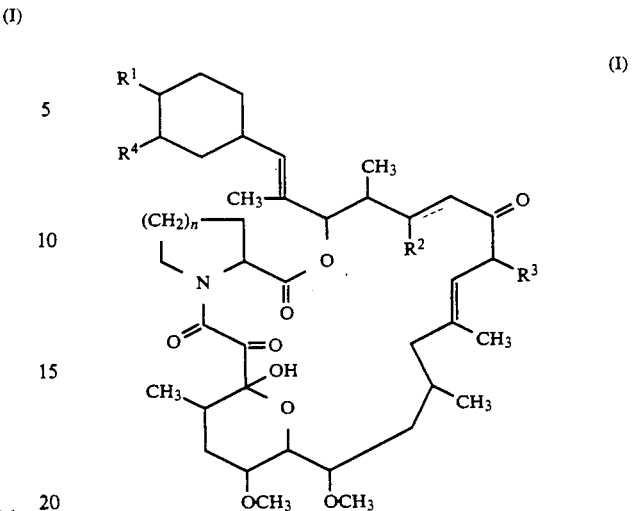 (I)

wherein $R^1$ is hydroxy or pharmaceutically acceptable protected hydroxy, $R^2$ is hydrogen, hydroxy or pharmaceutically acceptable protected hydroxy, $R^3$ is methyl, ethyl, propyl or allyl, $R^4$ is hydroxy, methoxy or oxo, n is 1 or 2 and the symbol of a line and a dotted line is a single bond or a double bond, provided that $R^2$ is not pharmaceutially acceptable protected hydroxy where $R^4$ is hydroxy or oxo, wherein said pharmaceutically acceptable protected hydroxy is selected from the group consisting of 1-(lower alkylthio)(lower)alkoxy, tri(lower)alkylsilyloxy, lower alkyl-diphenylsilyloxy, pharmaceutically acceptable organic carboxylic acyloxy, pharmaceutically acceptable organic sulfonic acyloxy and pharmaceutically accceptable organic carbamic acyloxy, and salts thereof.

12. The method of claim 11, wherein $R^1$ and $R^2$ are each hydroxy.

13. The method of claim 12, wherein $R^3$ is allyl.

14. The method of claim 11, wherein $R^3$ is ethyl.

15. The method of claim 11, wherein $R^3$ is methyl.

16. The method of claim 11, wherein $R^4$ is hydroxy.

17. The method of claim 11, wherein $R^4$ is methoxy.

18. The method of claim 11, wherein $R^4$ is oxo.

19. The method of claim 13, wherein the macrolide is FK 506.

20. A method for treating hepatic disease or liver resection by regenerating liver tissue, comprising administering to a mammal in need thereof, an effective amount of a macrolide of the formula shown below,

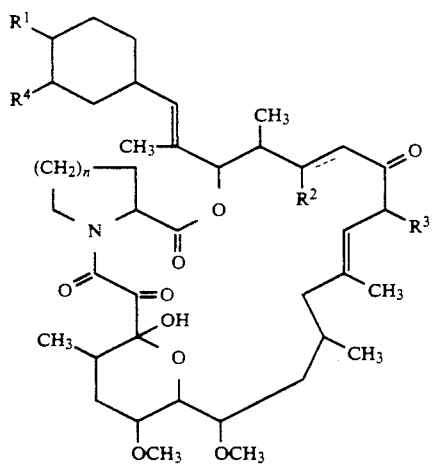 (I)

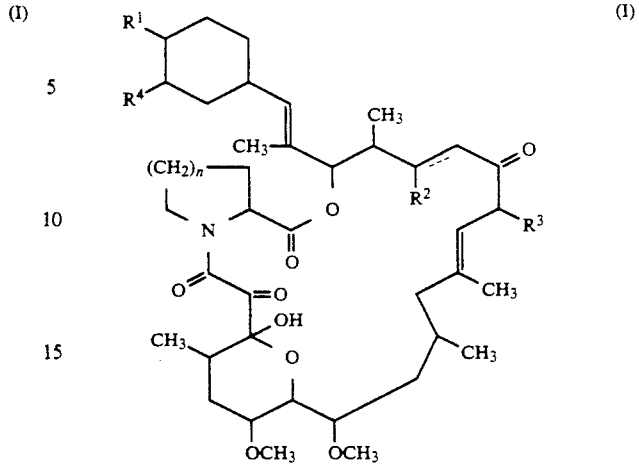 (I)

wherein $R^1$ is hydroxy or pharmaceutically acceptable protected hydroxy, $R^2$ is hydrogen, hydroxy or pharmaceutically acceptable protected hydroxy, $R^3$ is methyl, ethyl, propyl or allyl, $R^4$ is hydroxy, methoxy or oxo, n is 1 or 2 and the symbol of a line and a dotted line is a single bond or a double bond, provided that $R^2$ is not pharmaceutically acceptable protected hydroxy where $R^4$ is hydroxy or oxo, wherein said pharmaceutically acceptable protected hydroxy is selected from the group consisting of 1-(lower alkylthio)(lower)alkoxy, tri(lower)alkylsilyloxy, lower alkyl-diphenylsilyloxy, pharmaceutically acceptable organic carboxylic acyloxy, pharmaceutically acceptable organic sulfonic acyloxy and pharmaceutically acceptable organic carbamic acyloxy, and salts thereof.

21. The method of claim 20, wherein said hepatic disease is an immunogenic disease.

22. The method of claim 21, wherein said hepatic immunogenic disease is a chronic autoimmune liver disease.

23. The method of claim 22, wherein said autoimmune liver disease is selected from the group consisting of autoimmune hepatitus, primary biliary cirrhosis and sclerosing cholangitis.

24. The method of claim 20, wherein said hepatic disease is acute liver necrosis.

25. The method of claim 24, wherein said acute liver necrosis is necrosis caused by toxins, viral hepatitis, shock or anoxia.

26. The method of claim 20, wherein said administering step is oral, parenteral, enteral, intramuscular or intravenous administration.

27. The method of claim 26 wherein said administering is oral administration.

28. The method of any one of claims 20 to 25, 26 and 27, wherein the macrolide is FK 506.

29. A method for treating hepatic disease selected from the group consisting of B-virus hepatitis, non-A/non-B hepatitis and cirrhosis, comprising administering to a mammal in need thereof, a liver regenerating effective amount of a macrolide of the formula shown below:

wherein $R^1$ is hydroxy or pharmaceutically acceptable protected hydroxy, $R^2$ is hydrogen, hydroxy or pharmaceutically acceptable protected hydroxy, $R^3$ is methyl, ethyl, propyl or allyl, $R^4$ is hydroxy, methoxy or oxo, n is 1 or 2 and the symbol of a line and a dotted line is a single bond or a double bond, provided that $R^2$ is not pharmaceutically acceptable protected hydroxy where $R^4$ is hydroxy or oxo, wherein said pharmaceutically acceptable protected hydroxy is selected from the group consisting of 1-(lower alkylthio)(lower)alkoxy, tri(lower)alkylsilyloxy, lower alkyl-diphenylsilyloxy, pharmaceutically acceptable organic carboxylic acyloxy, pharmaceutically acceptable organic sulfonic acyloxy and pharmaceutically acceptable organic carbamic acyloxy, and salts thereof.

30. The method of claim 29, wherein said cirrhosis is alcoholic cirrhosis.

31. The method of claim 1, 11, 20 or 29, wherein said pharmaceutically acceptable protected hydroxy is selected from the group consisting of $C_1$-$C_4$-alkylthiomethyloxy, tri($C_1$-$C_4$)alkoxysilyloxy, $C_1$-$C_4$-alkyldiphenylsilyloxy, $C_1$-$C_4$-alkanoyloxy, carboxy substituted ($C_1$-$C_4$) alkanoyloxy, cyclo($C_5$-$C_6$)-alkyloxy($C_1$-$C_4$)alkanoyloxy having two $C_1$-$C_4$ alkyl groups on the cycloalkyl moiety, camphorsulfonyloxy, carboxy($C_1$-$C_4$)alkylcarbamoyloxy, tri($C_1$-$C_4$)alkylsilyl(-$C_1$-$C_4$)alkoxycarbonyl-($C_1$-$C_4$)alkylcarbamoyloxy, benzoyloxy, benzoyloxy substituted with one or two nitro groups, benzenesulfonyloxy, halogen substituted benzenesulfonyloxy, phenyl($C_1$-$C_4$)alkanoyloxy, and phenyl($C_1$-$C_4$)alkanoyloxy substituted with $C_1$-$C_4$ alkoxy or trihalo ($C_1$-$C_4$) alkyl groups.

32. The method of claim 31, wherein said pharmaceutically acceptable protected hydroxy is selected from the group consisting of methylthiomethyloxy, tert-butyl-dimethylsilyloxy, tert-butyl-diphenylsilyloxy, acetyloxy, carboxypropionyloxy, menthyloxyacetyloxy, camphorsulfonyloxy, benzoyloxy, nitrobenzoyloxy, dinitrobenzoyloxy, iodobenzenesulfonyloxy and 2-trifluoromethyl-2-methoxy-2-phenylacetyloxy.

* * * * *